US006396581B1

(12) United States Patent
Hayashi et al.

(10) Patent No.: US 6,396,581 B1
(45) Date of Patent: May 28, 2002

(54) SCANNER TYPE FLUORESCENCE DETECTION APPARATUS FOR TREATING NUMEROUS SAMPLES

(75) Inventors: Toshinori Hayashi; Takahiko Ishiguro, both of Kanagawa (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/492,302

(22) Filed: Jan. 27, 2000

(30) Foreign Application Priority Data

Jan. 27, 1999 (JP) .......................................... 11-018054

(51) Int. Cl.$^7$ .............................................. G01N 21/64
(52) U.S. Cl. ...................... 356/318; 356/417; 250/458.1
(58) Field of Search ................................. 356/317, 318, 356/417; 250/458.1, 458.9, 461.1, 461.2

(56) References Cited

U.S. PATENT DOCUMENTS

| | | | |
|---|---|---|---|
| 4,047,820 A | 9/1977 | Soodak et al. | 356/244 |
| 4,234,540 A | 11/1980 | Ginsberg et al. | 356/246 |
| 4,285,906 A | 8/1981 | Meltzer et al. | 356/435 |
| 4,329,061 A | 5/1982 | Snook et al. | 356/414 |

FOREIGN PATENT DOCUMENTS

| | | |
|---|---|---|
| DE | 24 32 624 | 4/1975 |
| FR | 2 622 305 | 4/1989 |
| WO | WO 83/03900 | 10/1983 |

Primary Examiner—F. L. Evans
(74) Attorney, Agent, or Firm—Sughrue Mion, PLLC

(57) ABSTRACT

A fluorescence detection apparatus is provided which comprises a sample holder for holding stationarily sample vessels deployed along a circle line or concentric circle lines having different radiuses, a partition plate connected to a driving means to be rotatable around the center of the circle line or concentric circle lines, an optical means for excitation light and an optical means for fluorescence light fixed respectively to the partition plate to be rotatable in integration therewith, a first light guide constituted of numerous optical fibers, a photosensor, and a light source for generating the excitation light, wherein the partition plate, the optical means for excitation light, and the optical means for fluorescence are integrally rotated, and thereby the fluorescence of the sample arranged along the circle line is successively detected and the detected fluorescence is transmitted to the photosensor. This fluorescence detection apparatus is useful in real-time monitoring of fluorescence signals, and satisfies the requirements of precise temperature control, quick treatment of many samples, high sensitivity, high reliability, low cost, and small size of the apparatus.

7 Claims, 9 Drawing Sheets

Plan view

Front view (partially in cross section)

Plan view

Front view (partially in cross section)

Enlarged view of temperature-controlling means (2:1)

Front view (partially in cross section)

SCANNER TYPE FLUORESCENCE DETECTION APPARATUS FOR TREATING NUMEROUS SAMPLES

BACKGROUND OF THE INVENTION

1. Field of the Invention

The present invention relates to a scanner type fluorescence detection apparatus for detecting fluorescence signals emitted from a specific substance in a sample and determining quantitatively the substance from the quantity of the detected signals. Particularly, the present invention relates to a scanner type fluorescence detection apparatus which is useful for real-time monitoring (monitoring of the change with time of the fluorescence signal quantity) of numerous samples in clinical diagnosis, like samples incubated at a prescribed temperature in an enzyme reaction or a like reaction.

2. Description of the Related Art

For real-time monitoring of the progress of formation of a fluorescent product in an enzymatic reaction, for example, the fluorescence from the sample is detected while the sample (liquid reaction mixture) is being incubated at a prescribed temperature. In clinical diagnosis, the detection should be conducted rapidly for a large number of samples simultaneously.

In a first method employed conventionally in clinical diagnosis, the samples are conveyed along a temperature-controlled guide and the fluorescence is detected successively. For example, a guide is made of a highly heat-conductive material like an aluminum alloy; the temperature of the guide is controlled by a heater or a like means; the samples are conveyed one by one or in plural at a time successively by a chain, a turn table, or the like along the guide; and the fluorescence signal is detected successively by a fluorescence detector arranged along the guide.

In a second method, for example, a connected sample vessel or a titer plate which is capable of holding numerous samples is placed on a temperature-controlling means, and the fluorescence of the numerous samples is detected simultaneously. Such a system is characterized by (1) plural photosensors, (2) a multi-channel type photosensor, or (3) a mechanical moving means for moving a photosensor or a light guide (a means for introducing the fluorescence signals emitted from the sample vessels) such as optical fibers.

The apparatus employing the plural photosensors (1) requires photosensors in number corresponding to the number of the samples to be detected simultaneously, and the fluorescence signals are detected separately for the respective samples. In such a system generally, the excitation light is split and the split rays are introduced through light guides to the respective samples.

The aforementioned multi-channel type photosensor (2) employs an image sensor such as a CCD and a photodiode array instead of the plural photosensors. The image sensor detects the fluorescence signals emitted by the arrayed samples are detected as an image with retention of the light-emitting positional relations. In such a system also, the excitation light is generally split and the split rays are introduced through light guides (optical instrument or optical fibers) to the respective samples.

The aforementioned mechanical moving means (3) moves a photosensor mechanically over the plural samples, or moves the respective samples successively to the fluorescence detection position where the fluorescence is detected by the photosensor. In such a system frequently, a light guide is moved mechanically. In this constitution, a light guide for the excitation light and another light guide for the fluorescence are employed and the sample sides of the both guides are combined and are moved together to excite the samples and detect the fluorescence therefrom successively.

For solving the problems mentioned later which are involved in the above systems, another scanner type fluorescence detection apparatus is disclosed in Japanese Patent Application No. 10-254913. In this apparatus, as shown in FIG. 3, sample vessels are deployed and arranged along a circle line, and a ring portion of a ring-shaped light guide is opposed close thereto with interposition of a partition plate. An optical means for excitation light and an optical means for fluorescence light are fixed to the partition plate, and are rotated together with the partition plate. Fluorescence signals collected from the respective samples are transmitted through the ring-shaped light guide to the photosensor.

Conventional fluorescence detection apparatuses have the problems mentioned below in the real-time monitoring of the change with time of fluorescence emitted from a specified substance contained in a sample incubated at a prescribed temperature.

The aforementioned first method, in which the samples are conveyed along a temperature-controlled guide and the fluorescence is successively detected, may cause insufficient temperature-control accuracy, limitation of the speed of the treatment of a number of samples, and carry-over (contamination of the samples by sample splashing), disadvantageously. In other words, it is difficult to keep the entire of the sample delivery guide at a uniform temperature and to make uniform the thermal conduction between the delivery guide and the samples throughout the guide. Consequently, the temperature of the samples may vary during the delivery, or may differ between the samples. Further, in this method, in monitoring the change of the fluorescence signals for a long time, the same samples are delivered repeatedly, the fluorescence of the delivered samples is detected one by one successively, thereby the number of the treated samples being limited. Moreover, the carry-over cannot be prevented completely.

The aforementioned second method may cause different problems although the problems caused in the first method are solved.

The method employing the plural photosensors (1) requires high cost owing to the plural photosensors, and an installation space corresponding thereto. For size reduction of the apparatus, the number of the photosensors should be reduced for the limited installation space, which limits the number of the sample treated at one time. A photosensor of a small size such as a photodiode has not sufficient sensitivity to the faint fluorescence. The plural photodiodes should be calibrated individually. Further, since the intensity of the fluorescence signal is proportional to the intensity of the excitation light, the splitting of the excitation light from the light source will lower the detection sensitivity.

The method employing the multi-channel type photosensor (2) is not suitable because of low sensitivity to faint fluorescent light. To raise the sensitivity, an element (so-called image intensifier or the like) can be employed which amplifies the light quantity through electronic amplification by a micro-channel plate. However, this is extremely costly and is used only in special researches. Furthermore, this system detects the fluorescence over a broad range as an image, which may give rise to disadvantages of nonuniformity of light quantity detection caused by lens aberration and the additional treatment of an enormous amount of data.

The method employing the mechanical movement means (3) is restricted in movement range of the light guide by the limitation by flexibility of the light guide and may cause disconnection. In this method, the light transmission efficiency of the light guide is varied by flection, which makes difficult the detection of fluorescence with high reproducibility. The mechanical movement of the photosensor is also limited in the movement range by the attached cables, and the cable may cause disconnection.

The scanner type fluorescence detection apparatus disclosed in aforementioned Japanese Patent Application No. 10-254913, which solves the above problems, becomes larger in size of the apparatus and higher in cost with the increase of the number of the sample vessels to be held, disadvantageously. Specifically, the ring-shaped input end is counterposed close to the sample vessels arranged along a circle line with interposition of a partition plate. Therefore, the diameter of the ring constituted of optical fibers should be made larger with the increase of the number of the held sample vessels, requiring a larger number of the employed optical fibers. Further, the fluorescence signal output end of the light guide is also made thicker, which enlarges the areas of fluorescence wavelength selection means such as the light sensing face of the photosensor and an interference filter. The larger sizes and higher cost of the light guide, the photosensor, interference filter, and other optical means result in significant larger size and higher cost as a whole.

As described above, the fluorescence detection apparatus for real-time monitoring of fluorescence signals, especially for real-time monitoring of samples incubated at a prescribed temperature, should satisfy the requirements of (A) precise temperature control, (B) quick treatment of many samples, (C) high sensitivity, (D) high reliability (less mechanical trouble such as disconnection and failure of movable parts, higher reproducibility in fluorescence detection, low possibility of carry-over), (E) lower cost (simpler constitution of the apparatus, use of less expensive parts for data treatment, etc.), and (F) a smaller size of the apparatus.

SUMMARY OF THE INVENTION

The present invention intends to provide a fluorescence detection apparatus satisfying the aforementioned requirements. Specifically the present invention intends to provide a fluorescence detection apparatus for real-time monitoring of stationarily held numerous samples without increase of the size and cost of the apparatus for a larger number of the treated samples. The present invention intends further to provide the fluorescence detection apparatus having additionally an incubation function.

The fluorescence detection apparatus of the present invention comprises a sample holder for holding stationarily sample vessels deployed along a circle line or concentric circle lines having different radiuses, a partition plate connected to a driving means to be rotatable around the center of the circle line or concentric circle lines, an optical means for excitation light and an optical means for fluorescence light fixed respectively to the partition plate to be rotatable in integration therewith, a first light guide constituted of numerous optical fibers, a photosensor, and a light source for generating the excitation light, wherein (a) the optical means for excitation light is placed to introduce the excitation light from the side of the rotation center of the partition plate to excite selectively a sample in one of the sample vessels, (b) the optical means of fluorescence are provided in number of the circle lines having different diameters for arrangement of the sample vessels, and have respectively at least one second light guide to collect the fluorescence signals from the samples on the respective circle lines, (c) the optical fibers of the first light guide are deployed to confront the circular locus or loci drawn by fluorescence signal output ends of all of the optical means for fluorescence light on rotation of the shield plate, and are arranged densely to confront the photosensor at the fluorescence signal output end, and (d) the excitation light is successively introduced, with rotation of the partition plate, to the respective sample vessels arranged along the circle lines, and simultaneously the fluorescence is detected through the optical means for fluorescence light including the second light guide.

Another embodiment of the fluorescence detection apparatus has a single optical fiber or plural optical fibers as the second light guide.

Still another embodiment of the fluorescence detection apparatus of the present invention has the optical fiber constituting the first light guide deployed and arranged continuously in a ring form at the fluorescence signal input end, having the ring center on the shield plate.

A further embodiment of the present invention comprises an insulation vessel for housing at least the sample holder, and a temperature control means for keeping the samples at a prescribed temperature.

DETAILED DESCRIPTION OF THE PREFERRED EMBODIMENT

The embodiments of the florescence detection apparatus of the present invention are described in detail by reference to drawings.

Figure 1:
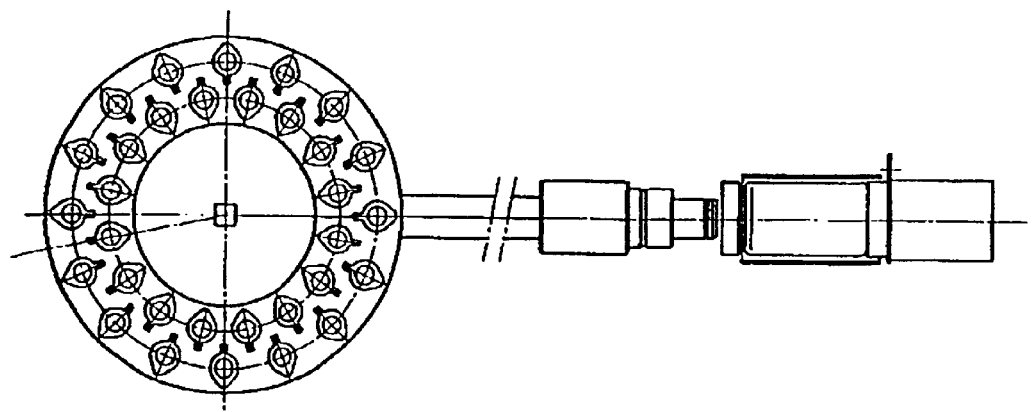
FIG. 1 shows schematically a fluorescence detection apparatus of the present invention.
Figure 1:
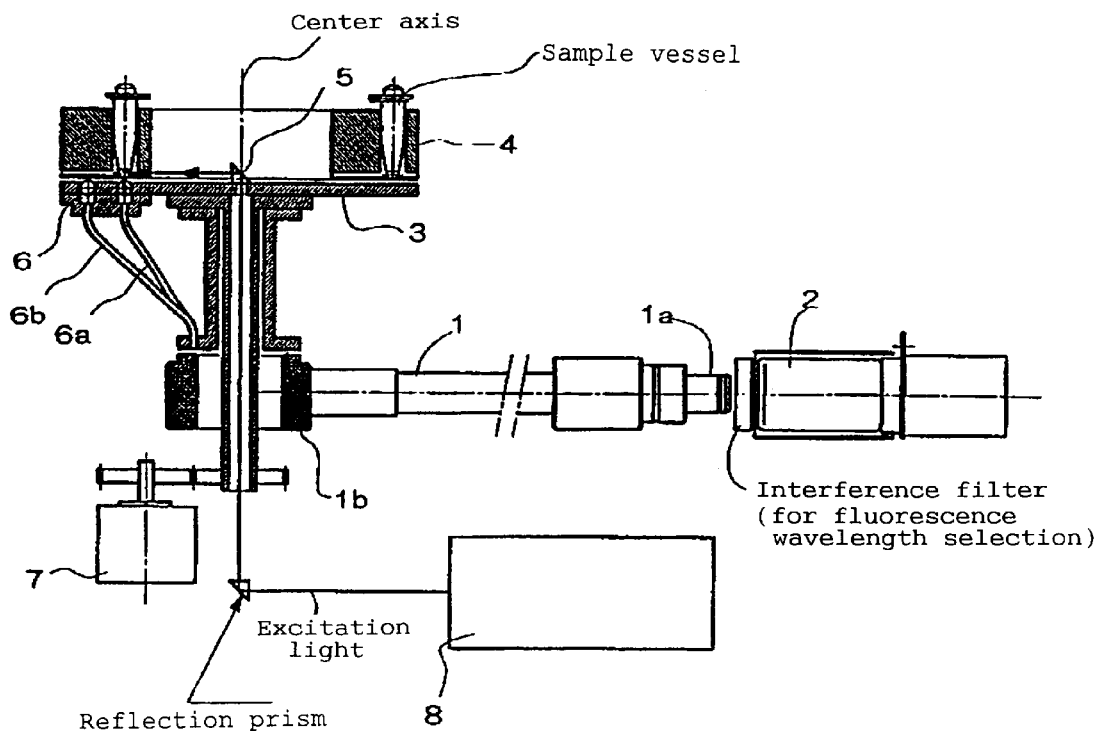

FIG. 1 shows a fluorescence detection apparatus set forth in claims 1–3, useful for real-time monitoring of numerous samples placed stationarily, employing an optical system for fluorescence analysis, without size increase and cost increase of the apparatus regardless of increase of number of the analysis treatment samples.

The sample holder 4 holds stationarily sample vessels deployed along two concentric circle lines of different radiuses. For holding the sample vessels, holding holes fitting to the outside shape of the sample vessel are provided along two circle lines. The sample vessels on the outside circle and the ones on the inside circle are held to face respectively to the center of the circles without interception. Thereby, a sample in one vessel can be excited by the excitation light introduced from the center side of the circles by the optical means for excitation light explained later without interception of the light path by another vessel, enabling individual excitation of all of the samples.

Incidentally, the arrangement of the sample vessels on the circle lines are not limited to be set in regular intervals or alternate to each other as shown in FIG. 1, provided that all of the sample vessels face to the center of the circles. The number of the sample vessels to be held by the sample holder is not limited and can be decided depending on the length of the circle lines and the outside diameter of the sample vessel. The shape of the sample holder viewed from the upside is not limited to be circular, but may be in a polygonal shape like a square.

The sample vessel may be made of any material, provided that the material is transparent to the excitation light and the fluorescent light and is stable chemically to the sample to be contained, and are selected in consideration of the sample size. In particular, in monitoring a reaction of enzymatic amplification of nucleic acids in PCR, NASBA, or a like reaction, a sample vessel having a sealing plug is preferred.

Under the stationarily fixed sample holder, a partition plate 3 is provided to be rotatable by a driving means 7 around the center of the circle line of the sample vessel arrangement. To the partition plate, an optical means 5 for excitation light and an optical means 6 for fluorescent light are fixed so as to be rotatable together with the partition plate.

The partition plate 3 is preferably constituted of a disk for a uniform rotation moment. The size (radius) of the partition plate 3 is at least not less than the distance between the center of the circle line and the sample vessels. The partition plate intercepts the fluorescent light path from the sample vessels to the first light guide except for the position (or part) of the optical means for fluorescence. The partition plate may be placed above the sample vessels. In this case, however, the partition plate should be made detachable for setting the sample vessels onto the sample holder. In many cases, the quantity of the sample is as small as several ten $\mu L$, and the efficiency of fluorescence detection is higher in receiving the fluorescence signal from the bottom of the sample vessel. Therefore, the partition plate is preferably placed under the sample holder.

The optical means 5 for excitation light fixed to the partition plate introduces the excitation light generated by a light source 8 selectively to only one of the sample vessels arranged along the circle line. In the system shown in FIG. 1, the optical means for excitation light is a reflection mirror 5 which deflects perpendicularly the optical path of the excitation light introduced from the light source 8 through a mirror into a hollow of the rotation axis of the partition plate. Incidentally, the above statement "to introduce the excitation light selectively to only one of the sample vessels" should not be strictly taken, but it signifies to introduce the excitation light intentionally to one sample vessel. For example, a slight quantity of the excitation light may be reflected by the outside wall of the selected sample vessel to another sample vessel without adverse effect. A convex lens or a like member may be combined to the optical means to parallelize the excitation light. Being different from the one shown in FIG. 1, a smaller excitation light source like a semiconductor laser or a light-emitting diode may be placed fixedly on the rotating partition plate to integrate the optical means for excitation light and the light source.

The optical means 6 for fluorescence light serves to introduce only the fluorescence light emitted from the one sample vessel irradiated with the excitation light to the first light guide 1. Accordingly, the fluorescence introducing end, and the fluorescence emitting end of the optical means for fluorescence are respectively placed to confront close the sample vessel and the first light guide.

This optical means for fluorescence light rotates together with the rotating partition plate. Therefore, in the case where the sample vessels are arranged along plural circle lines of different radiuses, the optical means should be provided fixedly in the same number as that of the circle lines. In the example shown in FIG. 1, two optical means for fluorescence should be provided, and the fluorescence signal input ends are placed fixedly to correspond respectively to the circle lines of sample vessel arrangement on a straight line perpendicular to the center axis. Thereby, the florescence only from the selected one sample can be collected separately whether the sample vessel is on the inner circle line or on the outer circle line.

The partition plate intercepts the fluorescence light from the other sample vessels, even if it is emitted, not to reach the first light guide and not to cause introduction of fluorescence signal from plural sample vessels to the photosensor. Thus, the fluorescence signals from numerous samples can be monitored intermittently in real time with only one photosensor.

Each of the optical means 6 for fluorescence light comprises a second light guide 6a or 6b which relays the fluorescence signals emitted from the sample vessel through a small hole or slit to the first light guide. Naturally, an optical part like a condenser lens may be inserted before or after the second light guide to condense the fluorescence signals. For the second light guide, flexible optical fibers are most suitable, but a rigid light guide may be used such as a single rod-shaped ones, single blade-shaped ones, and fused bundle of many fine optical fibers. With an optical fiber limited in bending curvature, or with a rigid light guide as the second light guide, a mirror, a prism or a like deflection element may be placed at one end or both ends of the second light guide.

The first light guide 1 is constituted of many optical fibers and serves to transmit the fluorescence signals emitted from the second light guide to the photosensor 2.

At the input end for the fluorescence signals of the first light guide, optical fibers, as constitutional elements, are deployed and arranged to face to the circular loci of fluorescence emitting ends of the two optical means 6 drawn by rotation of the partition plate 3. The range of the arrangement should cover the circular loci, but need not be the same in shape as the loci. Preferably the input ends are arranged without a gap in a shape of a circle of the same diameter as the circular locus. The two fluorescence signal output ends are preferably placed close to each other to make smaller the range of the optical fiber arrangement.

The fluorescence signal output end of the first light guide 1 is placed in opposition to a photosensor 2. The both are preferably fixed sufficiently close to each other to transmit the fluorescence signals emitted from the first light guide to the photosensor without decay. The ends of the respective optical fibers constituting the first light guide are preferably bundled by a suitable fittings to compact and true the end faces. By bundling the ends to make smaller the terminal area, the florescence signal can be received by a portion of relatively uniform sensitivity of the photosensor although the sensitivity of light receiving face of the photosensor is not always uniform.

A typical example of the first light guide is a ring type light guide used in an illumination device of an optical microscope. This ring type light guide is constituted of many optical fibers, the one end is arranged in a circular shape continuously, and the other end is bundled to be compacted and trued to meet the requirement described above. The ring portion of the ring type light guide is fixed with the center of the ring thereof placed at the rotation center axis of the partition plate.

The apparatus of the present invention has only one photosensor 2 to detect fluorescence of numerous samples. The fluorescence emitting end bundle is placed fixedly close to the photosensor 2. Between them, an optical filter may be placed for selecting the wavelength of fluorescence light necessary for the detection. Instead, the optical filter may be placed in front of the fluorescence signal input end, or as a portion of the optical means for fluorescence fixed to the partition plate.

The light source 8 is selected depending on the excitation wavelength of the sample, and in consideration of the necessary light intensity of the excitation light introduced to the sample vessel through the optical means for excitation light. The excitation light is preferably parallel rays or parallelized by a usual optical member. Specific example includes laser light sources such as an argon ion laser and a semiconductor laser, and light-emitting diode.

With the above constitution, in the system shown in FIG. 1, the excitation light is introduced to the sample vessels held stationarily on the sample holder successively one by one with rotation of the partition plate. Simultaneously, the fluorescence light emitted from the sample vessel is introduced through the optical means for fluorescence light comprising the second light guide to the first light guide, and is detected by the photosensor. Therefore, the intermittent fluorescence detection results of the samples held on the sample holder can be obtained by accumulating the detection results with the photosensor by controlling the rotation of the partition plate with a computer or the like, realizing real-time monitoring.

The second light guide employed as a part of the optical means for fluorescence makes it unnecessary to place the fluorescence signal input face of the first light guide 1 in close opposition to the sample vessels. Therefore, the ring type light guide of the first light guide can be made smaller irrespectively of the number of the held sample vessels. Moreover, even with a smaller diameter of the ring type light guide employed as the first light guide, the sample vessels can be deployed and arranged close together in a small range along plural concentric circle lines of different diameters. This can prevent increase of the size and the cost of the entire apparatus with the increase of the number of the held sample vessels advantageously.

FIG. 1 shows an example in which two circle lines of different diameters for arrangement of the sample vessels and two optical means for fluorescence are employed. However, as is clear from the description above, the number of the circle lines and the number of the optical means for fluorescence are not limited thereto, provided that the numbers of the both are the same and the respective sample vessels face to the center of the concentric circle lines.

Figure 2:
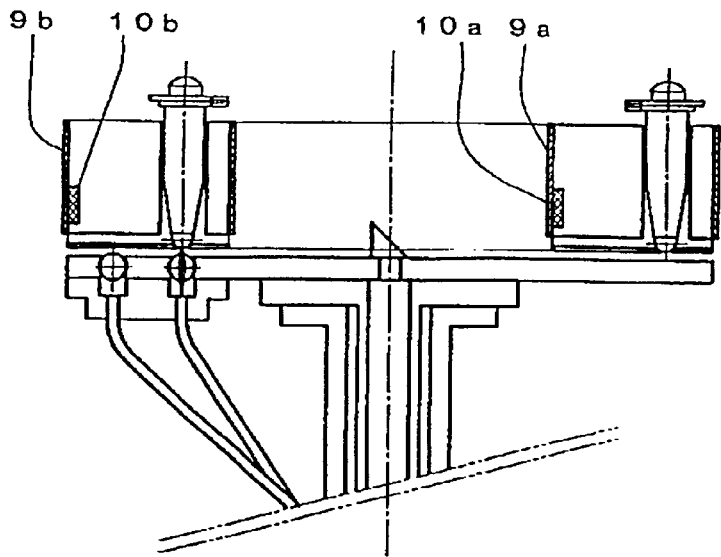
FIG. 2 shows schematically a fluorescence detection apparatus of the present invention equipped with a temperature control means.
Figure 2:
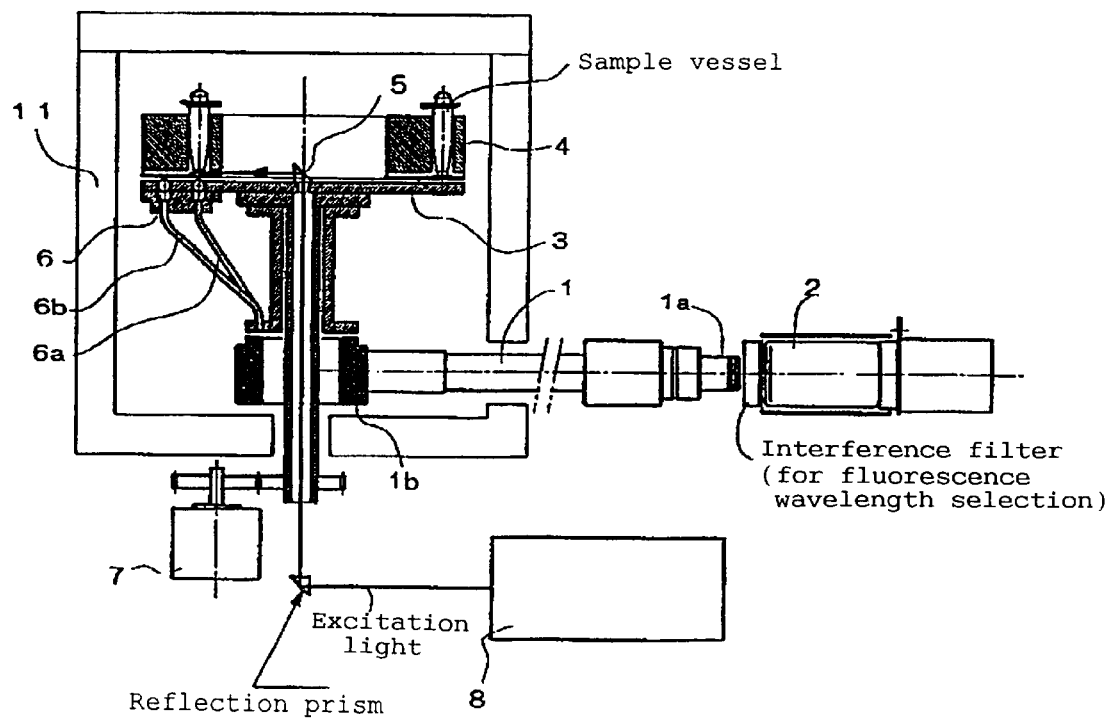
Figure 3:
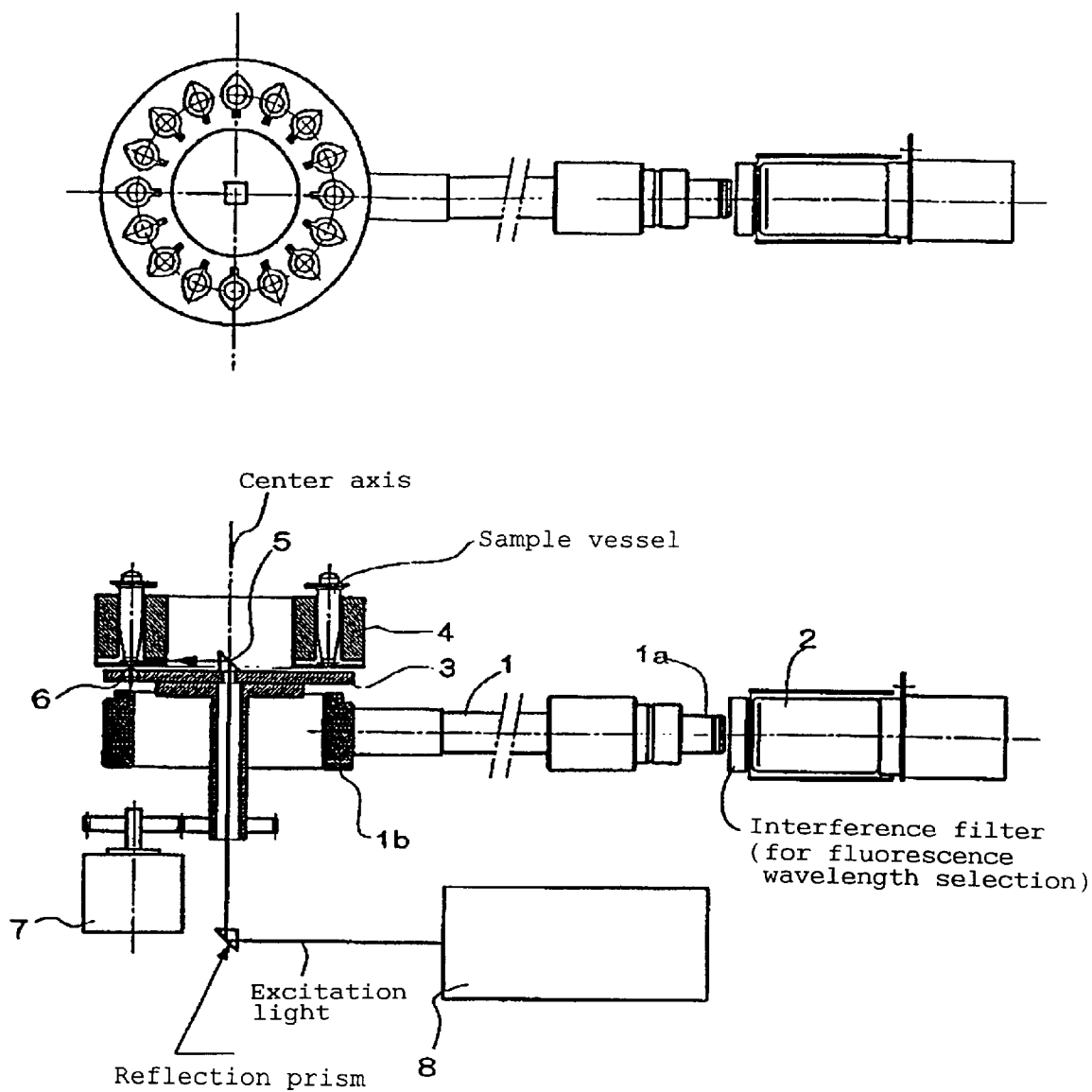
FIG. 3 shows schematically a conventional scanner type fluorescence detection apparatus.
Figure 4:
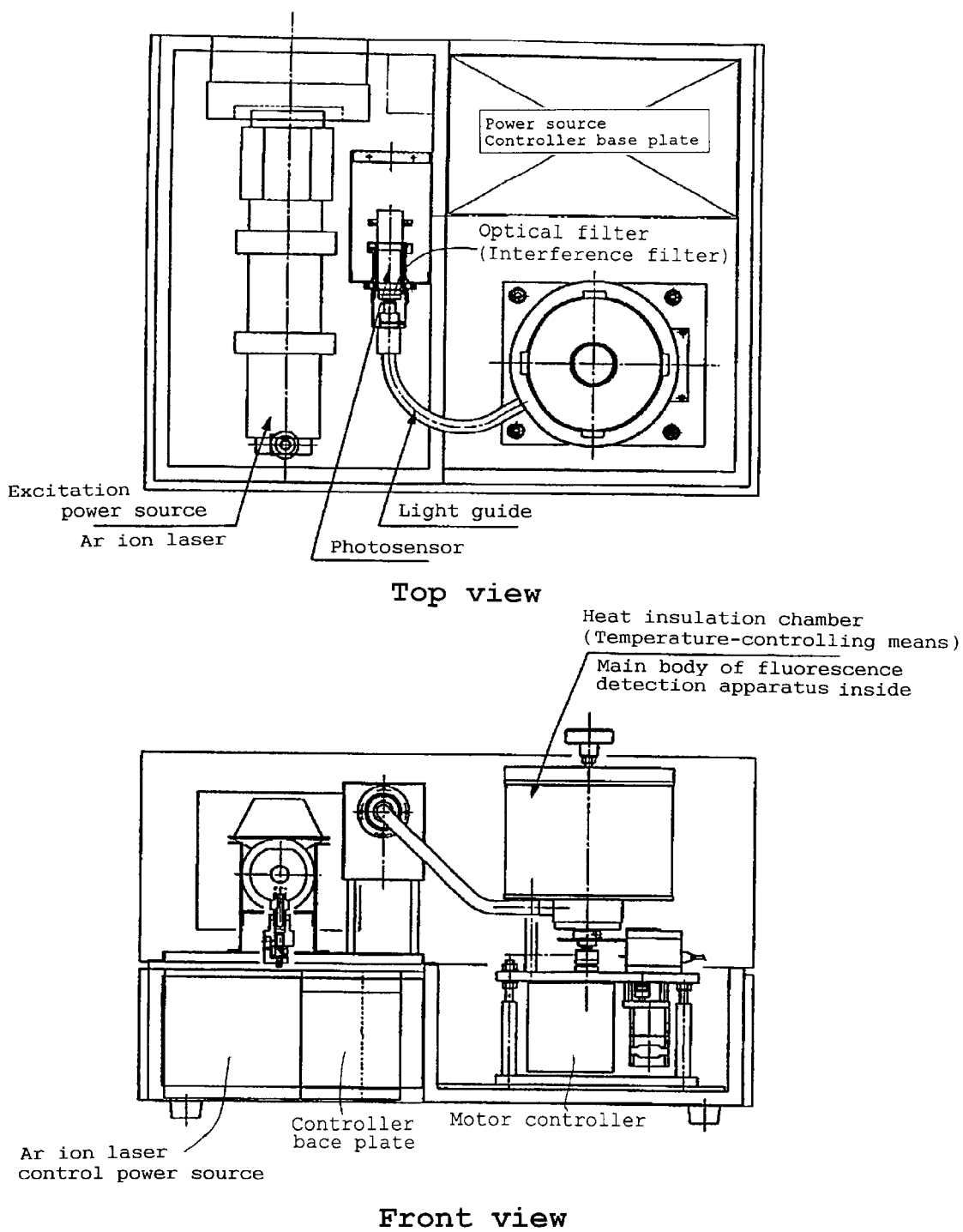
FIG. 4. shows schematically the entire of a fluorescence detection apparatus of an embodiment of the present invention.

FIG. 2 shows a fluorescence detection apparatus which is useful for real-time monitoring of numerous fixedly held samples, comprising an optical system for fluorescence analysis without size increase or cost increase with increase of the number of analysis treatment samples, and additionally a temperature-controlled incubation means, as one embodiment stated in claim 4. In other words, the apparatus shown in FIG. 2 has the optical system for fluorescence analysis explained by reference to FIG. 1 and additionally a temperature-controlling means for keeping the samples at a prescribed temperature.

The temperature-controlling means comprises a pair or pairs of a heater and a temperature sensor. The example shown in FIG. 2 comprises two pairs thereof. Plural pairs of the heater and the temperature controller are provided for keeping the sample vessels arranged along respective plural concentric circle lines at the same temperature. When the sample vessels are arranged along one circle line, one pair thereof functions satisfactorily since the distances between the one heater and the sample vessels can be made equal.

The sample holder is made in a round ring shape as viewed from the upside. One heater $9a$ or $9b$ and one temperature sensor $10a$ or $10b$ are attached respectively onto the inside circumference and the outside circumference of the sample holder. The heaters and the sensors are connected to temperature controllers, and the both sensors are set at the same temperature. Thereby the contact faces between the sample vessels and the sample holder are kept entirely at the same temperature to control the samples to be at the same temperature by thermal conduction from the sample holder.

The example in FIG. 2 has a heat insulation chamber for housing the sample holders, the partition plate and a portion of the rotation-driving means, the optical means for exciting light and the optical means for fluorescence light fixed to the partition plate, and the fluorescence signal input portion of the first light guide. The heat insulation chamber is preferably provided to insulate thermally the sample having the temperature controlled by the temperature-controller from the outside for more accurate temperature control. At least the sample holder is housed in the insulation chamber for that purpose.

The method of the temperature control is not limited to the above method. For example, the sample holder is placed in a thermostatic chamber and the temperature is controlled by air convection. The method of the temperature control is not limited to heating by a heater or the like, but may be cooling, or heat cycles of repeated heating and cooling. The cooling may be conducted by using a cooling element such as a Peltier element, and a cooling fan in place of the heater. The heat cycles are conducted by combined use of a heating element such as a heater, and a cooling element such as a Peltier element and a cooling fan.

By combination of the optical system shown in FIG. 1 and a temperature-controlling means, a fluorescence detection apparatus can be provided which is capable of conducting incubation at a prescribed temperature such as an enzyme reaction with numerous samples with high accuracy and monitoring the change with time of fluorescence signals resulting from the enzyme reaction in real time.

FIGS. 4–7 shows the fluorescence detection apparatuses of the present invention for detailed explanation without limiting the invention.

Figure 6:
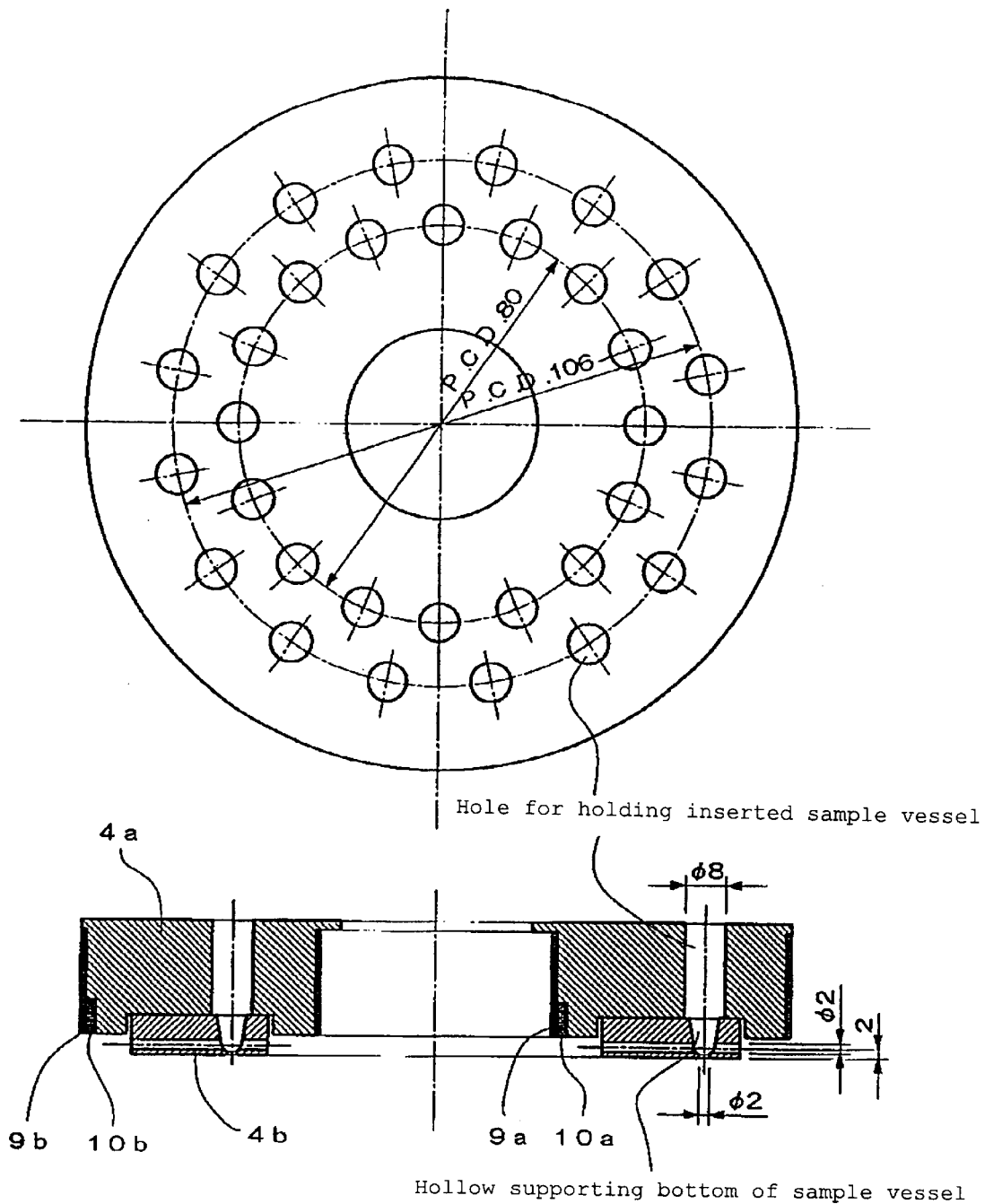
FIG. 6 is a sectional front view and a plan view of a sample holder portion and the temperature control means of the fluorescence detection apparatus shown in FIG. 4 for detailed description thereof.

FIG. 6 shows a sample holder 4. The sample holder 4 is constituted of two ring-shaped aluminum alloy parts: an upper part and a lower part. The upper ring-shaped part 4a has 32 holes (8 mm in diameter) fitting to the outside diameter of sample vessel for inserting and holding 32 sample vessels along two circle lines of diameters of 80 mm and 106 mm: 16 holes deployed at regular intervals on each of the circle lines. The holes along the inside circle line and the holes along the outside circle lines are arranged alternately to allow the respective holes to face the center axis of the partition plate. The lower ring-shaped part 4b has 32 hollows for contact-supporting respectively the bottom of the sample vessel, 32 holes of 2 mm in diameter for passing of excitation light, and 16 holes of 2 mm in diameter for collecting fluorescence signals at positions corresponding to the 32 holes of the upper ring-shaped part.

Figure 7:
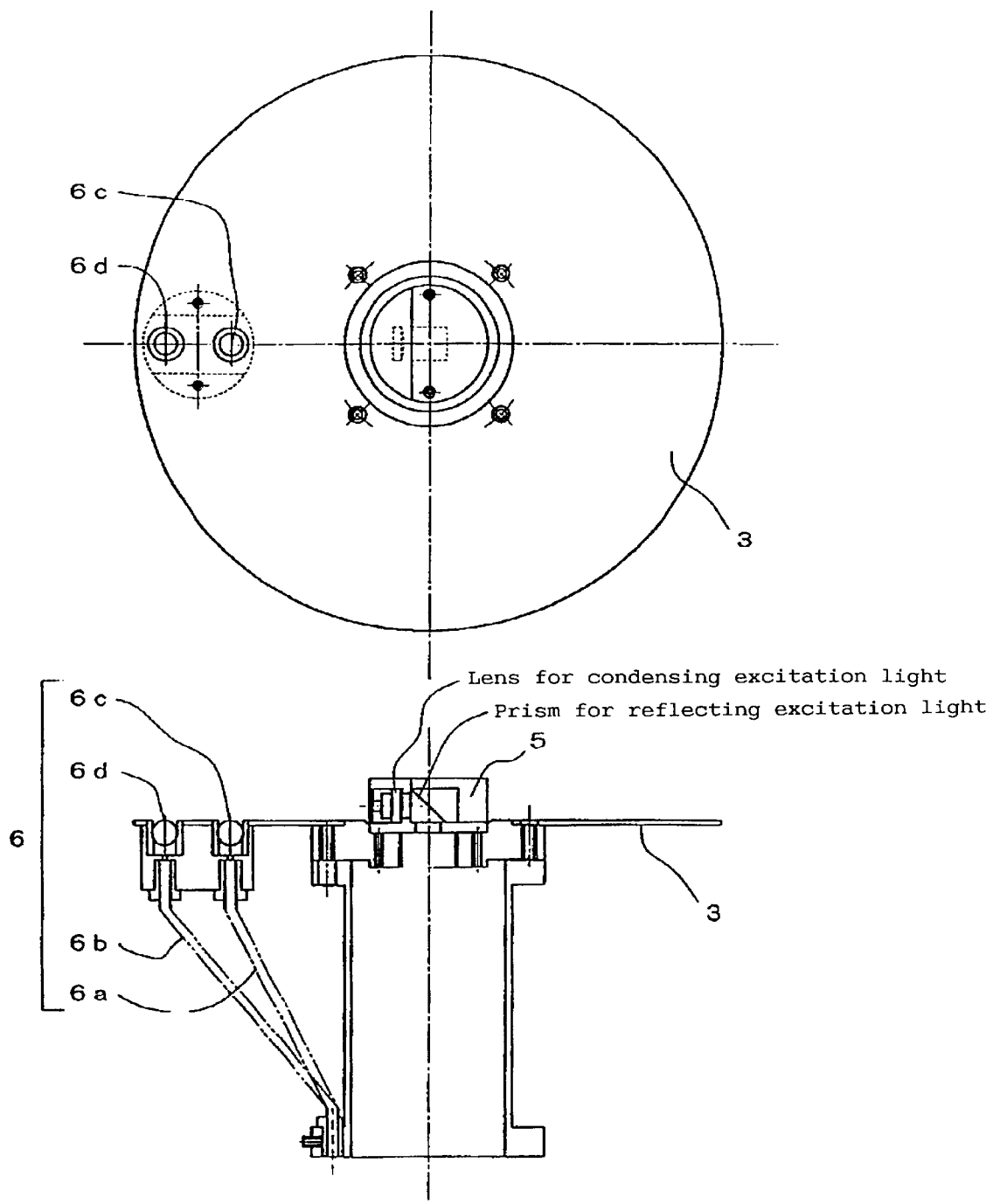
FIG. 7 is a sectional front view of a shield plate and an optical means for excitation light and an optical means for fluorescence fixed to the shield plate for detailed description thereof.

Below the sample holder, a disk-shaped partition plate 3 is placed close to the sample vessels as shown in FIG. 7. At the center portion of this partition plate 3, a rectangular prism is placed fixedly as an optical means 5 for excitation light to reflect rectangularly the excitation light introduced upward along the rotation axis to introduce it to one sample vessel. At the outer peripheral portion of the partition plate 3, two holes are bored for transmission of the fluorescent signals, and there, two optical means 6 for fluorescence comprising ball lenses 6c,6d and second light guides 6a,6b are placed fixedly. The two holes and the fluorescence signal input ends of the two optical means for fluorescence are respectively counterposed to the two circle lines of sample vessel arrangement, and are placed fixedly on the line perpendicular to the center axis of the concentric circle lines. In this example, the second light guides 6a,6b are formed from plastic optical fibers (1 mm in fiber diameter, about 80 mm in length). The two fluorescence signal output ends are brought close to each other, are counterposed to the fluorescence signal input ends of the first light guide, and connected fixedly to the rotation axis of the partition plate.

Figure 5:
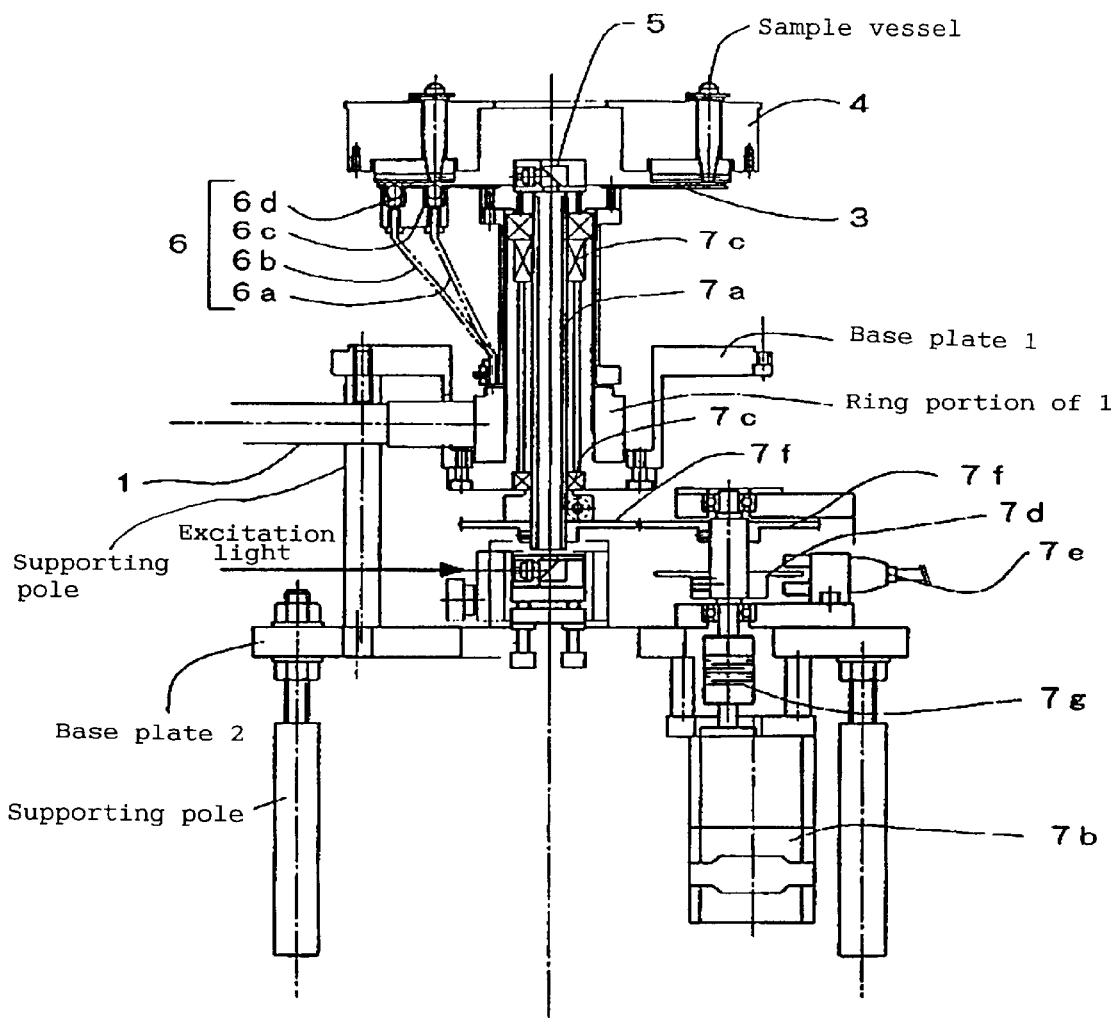
FIG. 5 is a front view of a portion of the fluorescence detection apparatus shown in FIG. 4 for detailed description thereof.

To the partition plate 3, as shown in FIG. 5, the driving means 7 is connected which comprises cylindrical rotation axis 7a, a stepping motor 7b, a bearing 7c, a rotation slit 7d, a rotation position sensor 7e, transmission gear 7f, and a coupling 7g. Thereby, the partition plate 3, and the optical means 5 for excitation light and the optical means 6 for fluorescence light fixed thereto are rotated integrally by the movement of the driving means. A rotation slit and a rotation position sensor may be provided for confirmation of the state of the rotation of the partition plate, namely the position of the sample vessel just under the fluorescence detection.

Figure 8:
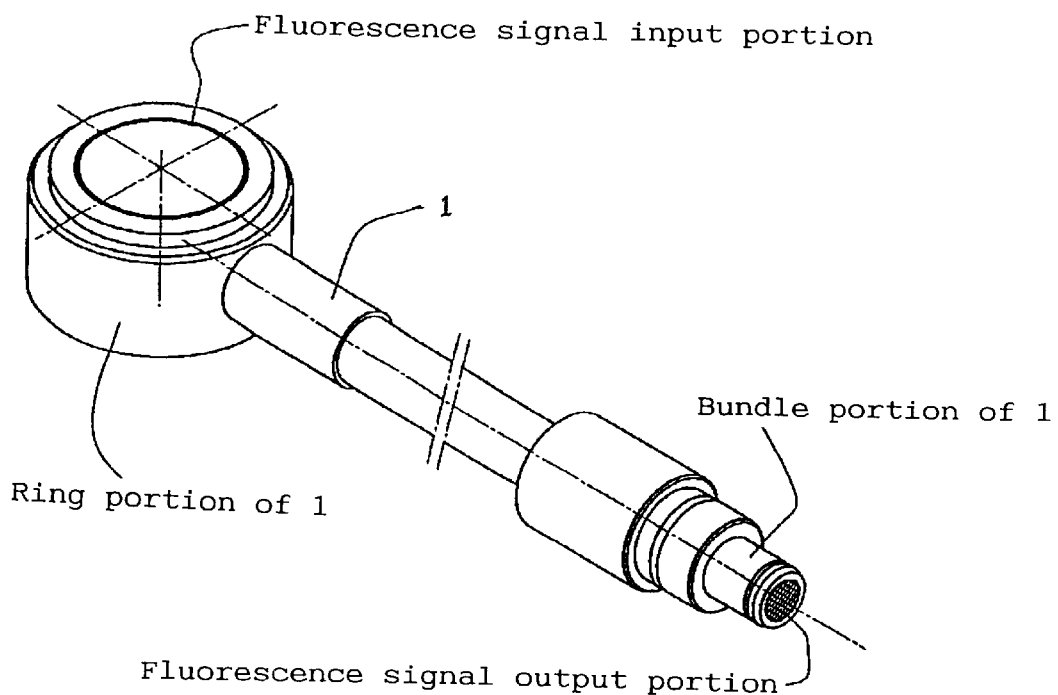
FIG. 8 shows an embodiment of the first light guide of the fluorescence detection apparatus shown in FIG. 4.
Figure 9:
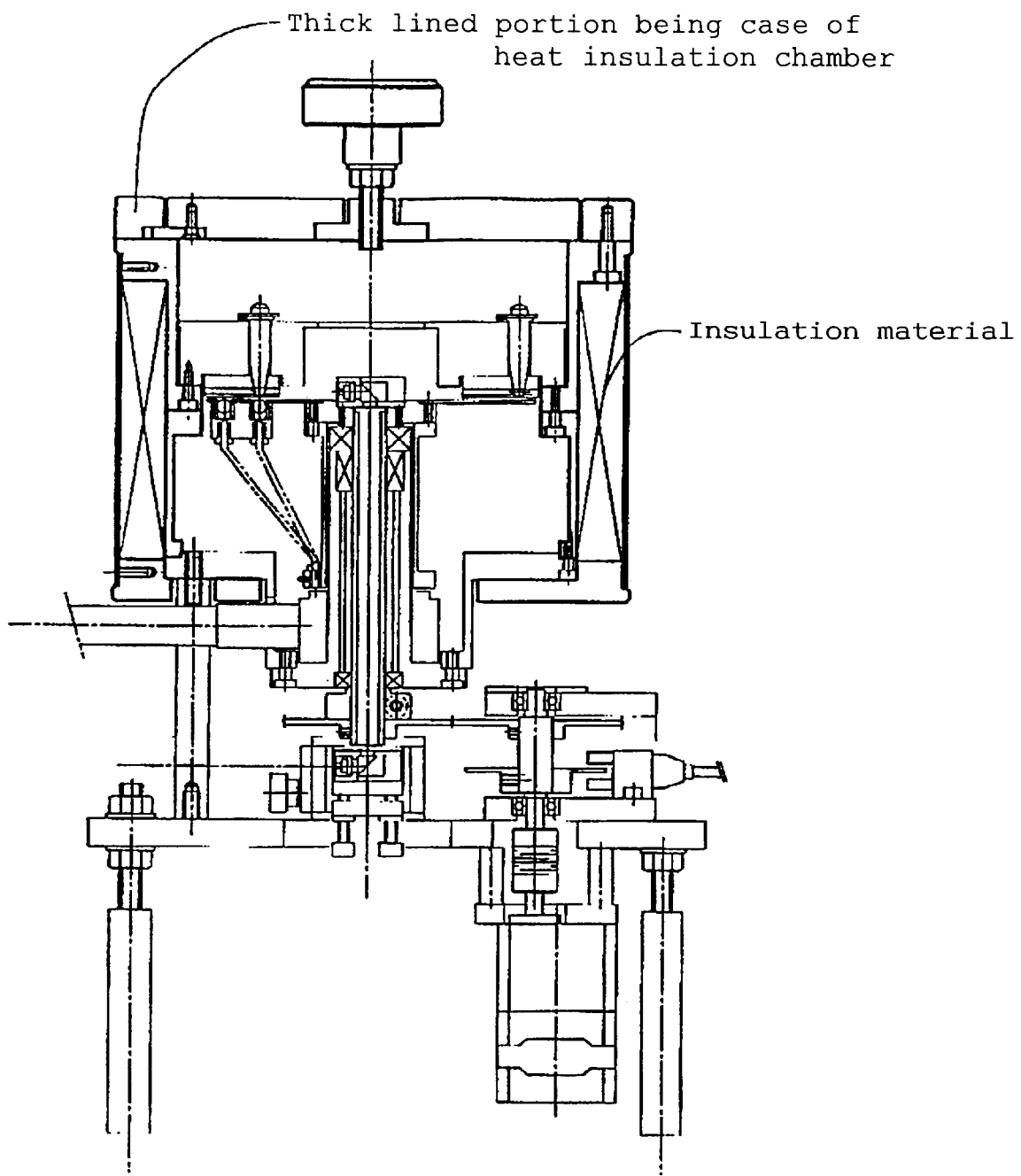
FIG. 9 is a sectional front view of a portion of the fluorescence detection apparatus shown in FIG. 4 for detail description of the heat insulation chamber of the temperature control means.

As the first light guide 1 constituted of a bundle of optical fibers, a ring type light guide as shown in FIG. 8 for illumination light transmission of optical microscope is employed in this example (fiber strand diameter: 30 μm, number of fiber strands: about 90,000, bundle diameter: 9.5 mm, ring diameter: 38 mm). This ring type light guide is usually used to illuminate the observation object of an optical microscope by emitting from the ring the light introduced from the bundle portion. In this example, the ring type light guide is used by reversing the direction of the light transmission, utilizing the ring portion as the fluorescence signal input end and the bundle portion as the signal output end.

The fluorescence signal input end of the first light guide 1, namely the ring portion, is placed fixedly such that the center of the ring is at the rotation axis of the partition plate, as shown in FIGS. 1 and 5. With the rotation of the partition plate, the fluorescence signal output end of the second light guide draws a circular locus. The two fluorescence signal output ends of the second light guides are opposed closely to the ring portion of the first light guide, so that the fluorescence signals outputted from the second light guide is introduced to the first light guide to be transmitted invariably to the photosensor irrespective of the state of the rotation of the partition plate.

At the fluorescence signal output end (bundle portion) of the ring type light guide, a photosensor (photomultiplier) is placed close thereto with interposition of an optical wavelength selection filter (interference filter: 520 nm). An argon ion laser is employed as the excitation light source, and the laser light of 488 nm is used as the excitation light.

A base plate 1, a base plate 2, and a supporting pole are designed to fix the positional relations of the parts for assembling the sample holder, the partition plate and rotation-driving mechanism, the optical means for excitation light and the optical means for fluorescence light fixed to the partition plate, and the ring portion of the first light guide of the aforementioned parts. The rectangular prism is set to be finely adjustable as the reflection mirror for introducing the excitation light emitted from the excitation light source along the rotation axis.

The sample holder is made in a round ring shape as viewed from the upside, as in FIG. 6. One heater 9a or 9b and one temperature sensor 10a or 10b are attached respectively onto the inside circumference and the outside circumference of the sample holder. A tape heater is used as the heater, and a platinum resistance thermometer is used as the temperature sensor. A heat insulation chamber houses the sample holder, the partition plate and a portion of the rotation-driving means, the optical means for exciting light and the optical means for fluorescence light fixed to the partition plate, and the fluorescence signal input portion of the first light guide. The heat insulation chamber is made of a material of low thermal conductivity such as a polyacetal type plastic material and polystyrene foam. By the thermal insulation, the temperature of the samples can be controlled precisely and an incubation faculty for enzymatic reaction or the like can be achieved.

The above-mentioned fluorescence detection apparatus detects the fluorescence signal by the process shown below. The laser beam emitted from the argon ion laser is reflected upward along the rotation axis by the reflection prism placed below the rotation axis. Then, the laser beam is reflected by the rectangular prism placed on the partition plate toward the sample vessel to excite the sample contained in the sample vessel. The fluorescence light generated by the sample is emitted from the lower portion of the sample holder, and is transmitted through the hole of the optical means for fluorescence light, condensing ball lens, and the second light guide to be condensed at the fluorescence input end (ring portion) of the first light guide. The fluorescence light transmitted through the first light guide is monochromated by the interference filter of 520 nm, and converted to electric signals by photomultiplier, and the electric signals are detected.

The 32 samples in the vessels, which are arranged fixedly along the two circle lines, are successively excited by the laser beam, and the generated fluorescence light is collected by the optical means for fluorescence light with the rotation of the partition plate. Thereby, numerous samples, 32 samples in this example, can readily be treated for fluorescence detection. By repeating the rotation of the partition plate for a long time, the change of the fluorescence signals of the samples with lapse of time can be monitored intermittently.

The fluorescence detection apparatus of the present invention has advantages below.

The temperature of sample vessels can be controlled precisely for quick treatment of numerous samples, since the sample holder for holding plural sample vessels is fixed stationarily. Temperature difference between the samples, and carry-over by shock or swing are prevented, since the sample vessels are fixed and not carried.

The signals can be detected with high sensitivity without noise increase by temperature rise, since the photosensor can be placed outside the equipped temperature-controlling means. The cost for the photosensor can be reduced, the apparatus can be made smaller, and troublesome operation of calibration of plural photosensors can be omitted, since only one photosensor is used. The work for data treatment can be simplified, since the change of the fluorescence signals of numerous samples can be detected by treating the signals from the only one photosensor. In particular, use of a photomultiplier as the photosensor gives extremely high sensitivity of the fluorescence detection apparatus sensitive to faint fluorescence signals.

The optical fibers of the first light guide is fixed stationarily in the present invention, and the second light guide is fixed to the partition plate to rotate with the shape kept unchanged without change of the flection state. Therefore, no change of the light transmittance efficiency is caused by change of the flection state of the optical fiber, consequently achieving high reproducibility of the signal detection.

In the apparatus of the present invention, only the partition plate and the optical members for excitation and fluorescence are moved mechanically. No cable is connected to the moving parts. Therefore, the movement range is not limited, cable disconnection is eliminated, and mechanical trouble is minimized. As described above, in the present invention, the sample vessels and light guides are not carried nor moved, but the shield plate and optical means are rotated to conduct real-time monitoring of numerous samples.

The scanner type fluorescence detection apparatus as shown in Japanese Patent Application No. 10-254913 has problems, with increase of the number of the set samples, of increase of the size and increase of the cost of the entire apparatus. The problems can be repressed to be less. This effect is remarkable in the case where the sample vessels are arranged along plural circle lines.

The present invention provides, as described above, a fluorescence detection apparatus which is capable of monitoring, in real time, samples being incubated at a prescribed temperature and which satisfies the requirements of (A) highly precise temperature control, (B) quick treatment of numerous samples, (C) high sensitivity, (D) high reliability (prevention of disconnection and mechanical troubles typified by failure of operation of movable parts, improved reproducibility of fluorescence detection, and prevention of carry-over), (E) lower cost (simplified apparatus constitution, no use of expensive parts in the data treatment, and (F) smaller size of the apparatus, and so forth.

What is claimed is:

1. A fluorescence detection apparatus, comprising a sample holder for holding stationarily sample vessels deployed along a circle line or concentric circle lines having different radiuses, a partition plate connected to a driving means to be rotatable around the center of the circle line or concentric circle lines, an optical means for excitation light and an optical means for fluorescence light fixed respectively to the partition plate to be rotatable in integration therewith, a first light guide constituted of numerous optical fibers, a photosensor, and a light source for generating the excitation light, wherein (a) the optical means for excitation light is placed to introduce the excitation light from the side of the rotation center of the partition plate to excite selectively a sample in one of the sample vessels, (b) the optical means of fluorescence are provided in numbers of the circle lines having different diameters for arrangement of the sample vessels, and have respectively at least one second light guide to collect the fluorescence signals from the samples on the respective circle lines, (c) the optical fibers of the first light guide are deployed to confront the circular locus or loci drawn by fluorescence signal output ends of all of the optical means for fluorescence light on rotation of the partition plate, and are arranged densely to confront the photosensor at the fluorescence signal output end, and (d) the excitation light is successively introduced, with rotation of the partition plate, to the respective sample vessels arranged along the circle lines, and simultaneously the fluorescence is detected through the optical means for fluorescence light including the second light guide.

2. The fluorescence detection apparatus according to claim 1, wherein the second light guide is constituted of a single optical fiber or plural optical fibers.

3. The fluorescence detection apparatus according to claim 1, wherein the optical fibers constituting the first light guide are deployed and arranged continuously in a ring form at the fluorescence signal input end, and the center of the ring is on the center of the partition plate.

4. The fluorescence detection apparatus according to claim 1, comprising a temperature control means for keeping the samples at a prescribed temperature.

5. The fluorescence detection apparatus according to claim 2, wherein the optical fibers constituting the first light guide are deployed and arranged continuously in a ring form at the fluorescence signal input end, and the center of the ring is on the center of the partition plate.

6. The fluorescence detection apparatus according to claim 2, comprising a temperature control means for keeping the samples at a prescribed temperature.

7. The fluorescence detection apparatus according to claim 3, comprising a temperature control means for keeping the samples at a prescribed temperature.

* * * * *